(12) United States Patent
Flatt

(10) Patent No.: US 7,558,738 B1
(45) Date of Patent: Jul. 7, 2009

(54) SOFTWARE ARTICLE, SYSTEM AND METHOD FOR PHYSICIAN REFERRAL SERVICES

(76) Inventor: Jerrold V. Flatt, 1301 Penn Ave., Suite 316, Des Moines, IA (US) 50316

(*) Notice: Subject to any disclaimer, the term of this patent is extended or adjusted under 35 U.S.C. 154(b) by 1752 days.

(21) Appl. No.: 09/992,764

(22) Filed: Nov. 6, 2001

Related U.S. Application Data

(60) Provisional application No. 60/246,241, filed on Nov. 6, 2000.

(51) Int. Cl.
*G06Q 50/00* (2006.01)
(52) U.S. Cl. .................................. 705/2; 705/3; 705/4
(58) Field of Classification Search ............... 705/2, 705/3, 4
See application file for complete search history.

(56) References Cited

U.S. PATENT DOCUMENTS

| | | | |
|---|---|---|---|
| 5,583,758 A * | 12/1996 | McIlroy et al. ................ | 705/2 |
| 5,924,074 A * | 7/1999 | Evans ............................ | 705/3 |
| 5,995,939 A | 11/1999 | Berman et al. | |
| 6,014,631 A * | 1/2000 | Teagarden et al. ............ | 705/3 |
| 2001/0034631 A1* | 10/2001 | Kiselik .......................... | 705/8 |
| 2001/0051881 A1* | 12/2001 | Filler ............................ | 705/3 |
| 2002/0082865 A1* | 6/2002 | Bianco et al. ................. | 705/2 |

* cited by examiner

*Primary Examiner*—Gerald J. O'Connor
*Assistant Examiner*—R. David Rines
(74) *Attorney, Agent, or Firm*—McKee, Voorhees & Sease, P.L.C.

(57) ABSTRACT

A system and method relating to managing patient referrals is disclosed. One method includes providing a web site accessible to a plurality of health care providers; receiving through the web site, a plurality of health care provider registrations each associated with a health care provider; receiving a request for a patient consultation from a first health care provider to be performed by a second health care provider, both the first health care provider and the second health care provider having a health care provider registration; and notifying the second health care provider of the request for a patient consultation.

22 Claims, 15 Drawing Sheets

PHYSICIAN REGISTRATION

PHYSICIAN INFORMATION     * - INDICATES REQ'D FIELDS

- *NAME: (FIRST, MI, LAST):
- *STREET ADDRESS:
- SUITE/APT#:
- *CITY/STATE:
- *ZIP CODE:
- *PHONE NUMBER: ( ) EXT.
- *FAX NUMBER: ( )
- MOBILE #: ( )
- PAGER #: ( )
- *EMAIL:
- *WEB URL:

PROFESSIONAL DETAILS

- *SPECIALTY:
- *SSN:
- *UPIN:
- *MEDICAL LICENSE:

LOGON INFO

PASSWORD:    CONFIRM:

( REGISTER PHYSICIAN NOW )

| CLINIC PROFILE | |
|---|---|
| CLINIC INFORMATION | |
| LOGON ID: ID1 | PASSWORD: PASS1 |
| CLINIC 1<br>ADDRESS<br>CITY,STATE ZIP | CONTACT: NAME |
| PHONE<br>FAX | EMAIL:<br>URL: |
| CREDIT CARD INFORMATION | |
| CARD TYPE: TYPE<br>NAME: NAME | CARD#: XXXX-XXX-XXX-XXXX<br>EXP. DATE: XX/XXXX |

(ADD NEW PHYSICIAN)

PHYSICIAN | DEPARTMENT | OPERATOR
LISTING

| NAME | SPECIALTY | | |
|---|---|---|---|
| DOCTOR 1 | VASCULAR SURGERY | EDIT | DELETE |
| PHONE 1 | INTERVENTIONAL GRAFTS | EDIT | DELETE |

*Fig. 4*

| CLINIC REGISTRATION | |
|---|---|
| CLINIC INFORMATION | |
| *OFFICE NAME: [ ] | GROUP: [ ] |
| SPECIALTY: [ ] | |
| * PASSWORD: [ ] | CONFIRM: [ ] |
| CLINIC DETAILS | |
| *CONTACT: (FIRST, MI, LAST): | [ ] [ ] [ ] |
| *STREET ADDRESS: | [ ] |
| *CITY/STATE: | [ ] [ ▼] |
| *ZIP CODE: | [ ] |
| *PHONE NUMBER: | ( [ ] ) [ ] EXT. [ ] |
| *FAX NUMBER: | ( [ ] ) [ ] |
| *EMAIL: | [ ] |
| *WEB URL: | [ ] |
| *DIRECTIONS TO OFFICE: | [ ] |
| CREDIT CARD DETAILS | |
| *CARD TYPE: | [ ▼] |
| *CARD#: | [ ] |
| *NAME ON CARD: | [ ] |
| *EXPIRATION DATE: | [ ] |
| (REGISTER CLINIC NOW) | |

*Fig. 5*

REQUEST A CONSULT

DOCTOR NAME
CLINIC         VASCULAR SURGEON
PHONE          EMAIL
FAX            URL

☑ FAX
☑ PAGER
☑ EMAIL (EDIT PROFILE)

— 84

PATIENT:       PATIENT NAME
SSN:           xxx-xx-xxxx
DOB:           xx/xx/xxxx
INSURANCE:     INSURER 1
               xxxxxxx
ADDRESS:       ADDRESS 1
               CITY, STATE ZIP
HOME:          (XXX)-xxx-xxxx
EMAIL:
OFFICE:        (XXX)-xxx-xxxx (VIEW DETAILS...)            (EDIT PATIENT)

— 82
SEARCH FOR PATIENT (?)

BY SSN:     [           ]  → GO
OR
BY NAME:    [           ]  → GO (ADD A NEW PATIENT)

CLINIC HOTLIST (?) — 86

| CLINIC/PHYSICIAN | SPECIALTY/OFFICE |
|---|---|
| CLINIC DOCTOR 2 | GENERAL MEDICINE CLINIC |

— 90

CLINIC: CLINIC NAME
PHYSICIAN: DOCTOR 2
SPECIALTY: GENERAL MEDICINE
           GERIATRICS

ADDRESS: ADDRESS 1
         CITY, STATE ZIP
HOME: (XXX)-XXX-XXXX
EMAIL:
OFFICE: (XXX)-XXX-XXXX (VIEW PROFILE...)  (VIEW CLINIC)

— 88

SEARCH FOR CLINIC: [      ] (↑) GO

OR (ADD A NEW PHYSICIAN)

③

URGENCY

REQUEST

COMMENTS

NOTIFY WITH ☑ FAX ☑ PAGER ☑ EMAIL (REFER PATIENT)

*Fig. 6C*

CONSULT NOTIFICATIONS   (UPON CONSULT REQUEST, NOTIFY MY...)

NOTIFY WITH | USING DURING                                    (EDIT)

☑ FAX  ☑ PAGER  ☑ EMAIL

DEPARTMENT OR PHYSICIAN

| WHEN ▲ | COMMENTS | | READ |
|---|---|---|---|
| 2:15 PM (XXX)-XXX-XXXX | VERY DILIGENT. PROFESSIONAL | RESPOND... | ☑ |
| 9:13 AM (XXX)-XXX-XXXX | POOR FOLLOW-UP NOT VERY TIMELY. | RESPOND... | ☑ |

| | RESPOND TO A CONSULT | | | |
|---|---|---|---|---|
| DOCTOR 1 | DEPARTMENT 1 | DOCTOR 2 | | CLINIC 1 |
| XX/XX/XXXX | ROUTINE | DOCTOR 2 | FAX IT | ELECTROCARDIOGRAM |
| XX/XX/XXXX | STAT | DOCTOR 2 | FAX IT | LAST EKG |

↙ 34

PATIENT DEMOGRAPHICS
PATIENT 1    BIRTHDATE
ADDRESS
CITY, STATE  ZIP

REQUESTING PHYSICIAN/CLINIC
DOCTOR 2    FAMILY PRACTICE
CLINIC 2    ADDRESS
PHONE    FAX    CITY,STATE  ZIP
WEB ADDRESS    ☐ FAX NOTIFY    ☐ EMAIL NOTIFY

REQUEST PREFERENCES: DATE AND TIME REQUEST MADE: XX/XX/XXXX    XX:XX:XX
URGENCY    REQUEST                        DATE REQUESTED INFO SENT:  XX/XX/XXXX
STAT
SEND BY    COMMENTS                       METHOD SENT:  FAXED ▼
FAX IT (DENY REQUEST)    (REQUEST COMPLETED)

*Fig. 9*

PATIENTS

NAME:
ADDRESS:
CITY: STATE ZIP
HOME PHONE WORK PHONE
FAX NUMBER EMAIL ADD:
BIRTHDATE AGE SSN
COMMENTS:

*Fig. 10*

SOFTWARE ARTICLE, SYSTEM AND METHOD FOR PHYSICIAN REFERRAL SERVICES

CROSS-REFERENCE TO RELATED APPLICATIONS

This application claims priority to provisional application Ser. No. 60/246,241 filed Nov. 6, 2000, herein incorporated by reference in its entirety.

BACKGROUND OF THE INVENTION

1. Field of the Invention

The present invention relates generally to healthcare services. More particularly, although not exclusive, the present invention relates to a software article, system and method for providing a healthcare referral and notification service.

2. Problems in the Art

The process of making physician referrals generally includes inefficient intra-office dialog, and information sharing between primary care physicians, clinics, hospitals, outpatient testing centers, specialists, and insurance companies. For example, a request from a primary care physician to a specialist or an outpatient testing center is a time consuming task for all involved, often requiring chart pulls, documentation, and call backs. Healthcare providers and clerical staff can find themselves in a "endless voicemail loop," on "hold" or playing "telephone tag."

There is no seamless communication between primary care physicians, consultants, outpatient testing facilities, hospitals, and insurance companies. The primary care physicians cannot quickly access information about referral options, consultant profiles, or information about an out-of-region tertiary care center. Office productivity suffers as a result. Simply put, the process of making a physician referral is inherently inefficient and costly.

Specifically, these inefficiencies are a result of a number of contributing factors. First, there are inadequate methods of tracking referrals, coordinating, and monitoring patient care between the primary care physician and a consultant. Further, the consultants do not know what the referring physicians preferences are for communication and feedback. This can result in the consultants selecting a mode of communication that is time consuming and inefficient or otherwise not preferred by the referring physician. For example, a consultant may communicate by telephone with the referring physician. The use of the telephone may be inconvenient and inefficient for the referring physician who prefers to be contacted only under certain circumstances by fax or e-mail. Another problem for primary care physicians is the difficulty in accessing or making referrals to regional or national healthcare providers. Many primary care healthcare providers, particularly those in rural areas, will need to make referrals to these types of providers, but may not have the proper contacts within these organizations or knowledge of particular physicians within these organizations.

A further problem for primary care physicians is that obtaining referral authorization numbers can be a complex and time consuming process. The primary care physician typically will need to provide ongoing office documentation concerning authorization.

Another problem involves the coordination of a referral with the patient. Presently, the patient may not be provided specific referral site information or directions to the site, or consultant information or testing information and preparation instructions, as the provision of such information would be difficult and time consuming for the primary care physician.

Thus, it can be seen that the referral process is time consuming, cumbersome, and expensive, particularly for the referring primary care physician. The lengthy process of coordinating the referral process with insurance companies and consultants is also problematic. Authorization codes from insurance companies are not provided in a seamless reliable fashion. Upon receiving a referral request, the consultant generally does not have the necessary patient demographic data, insurance information, contact information, and appointment preference information needed to complete the scheduling process. In sum, consultants (including specialists, outpatient care centers, hospitals, and insurance companies) face numerous problems.

These problems further include that there is no quick, simple, or accurate means of obtaining core data regarding a new consultation from a referring physician. There is no simple or accurate means to track and analyze referrals from others. There is no uniform electronic communications available to communicate between consultants and referring physicians. There is no simple means of obtaining referral authorization numbers. There is a need to enhance referral relations with referring physicians. There is a need for an ongoing dynamic referral relations analyst tool. There is a need or desire for greater exposure to the primary care base. And there is a need or desire for practice promotion and web awareness.

Therefore, it is a primary object, feature, or advantage of the present invention to provide a physician referral system that overcomes the problems and deficiencies in the prior art.

It is a further object, feature, or advantage of the present invention to provide an improved referral process that is less time consuming, less cumbersome, and less expensive than prior art solutions.

It is a further object, feature, or advantage of the present invention to provide a system and methods for tracking referrals that promote coordinating and monitoring of patient care.

Yet another object, feature, or advantage of the present invention is to provide system and methods for referrals that provide for communicating a preferred mode of communication and feedback between referring physicians and consultants.

A further object, feature, or advantage of the present invention is to provide a system and methods for referral that promotes a referring physician's ability to access or make referrals to regional or national healthcare providers.

A still further object, feature, or advantage of the present invention is to provide a system and methods for referral that allows for uniform electronic communication.

Another object, feature or advantage of the present invention is to provide a system and methods for referral that simplifies the process of providing patients with information about specific referral sites or directions to the site or consultant information or testing information and preparation instructions.

Yet another object, feature, or advantage of the present invention is to provide system and methods for referral that reduce the complexity and time required in obtaining referral authorization numbers.

Yet another object, feature, or advantage of the present invention is to provide a referral system and methods that enhance referral relations between referring physicians and consultants.

Yet another object, feature, or advantage of the present invention is to provide a system and methods of referral that provide for ongoing and dynamic analysis of referral relations.

A still further object, feature, or advantage of the present invention is to provide a system and methods of referral that increase a consultant's exposure to a primary care base.

A still further object, feature, or advantage of the present invention is to provide system and methods for referral that can be used to promote a particular medical practice.

Other objects, features, or advantages will become apparent from the disclosure that follows.

BRIEF SUMMARY OF THE INVENTION

The invention provides for novel systems and methods for managing patient referrals. The invention includes providing a web site accessible to a plurality of healthcare providers. Each of these healthcare providers, complete registrations that are received through the web site. The web site receives requests for patient consultations from a first healthcare provider to be provided by a second healthcare provider where both the first healthcare provider and the second healthcare provider are registered on the web site. Once this request is received, the second healthcare provider is notified of the request for a patient consultation. The second healthcare provider can accept or decline the request for patent consultation from the first heath care provider. The request can include information such as patient demographic data, insurance information, patient contact information, and appointment preference information. Based on this information, the second healthcare provider's availability, or for other reasons, the second healthcare provider then chooses to either accept or decline the request for patient consultation. If the request is accepted, the present invention further streamlines the process of communication between the referring healthcare provider and consulting healthcare provider.

The present invention also provides for a method of providing feedback to the consulting healthcare provider from the referring healthcare provider. This feedback can include a peer rating. The rating may be anonymous or it may be signed or otherwise attributed to the healthcare provider providing the feedback. The rating can include comments. This allows the consulting healthcare provider to monitor their performance and their relationships with referring healthcare providers.

The invention also provides for the web site to provide information about registered physicians, information about locating particular clinics, hospitals, or other healthcare centers. The invention also provides the opportunities for consulting healthcare providers to promote their practices.

The present invention provides for streamline communication between healthcare providers. In this manner, the invention allows basic information to be shared quickly, concisely and in a cost effective manner. The traditional use of telephones or faxes can even be eliminated.

BRIEF DESCRIPTION OF THE DRAWINGS

FIG. 3 is an illustration of a physician registration web page according to the present invention.

FIG. 4 is an illustration of a clinic profile web page according to the present invention.

FIG. 5 is an illustration of a clinic registration web page according to the present invention.

FIGS. 6A through 6C illustrate a "request a consult" web page according to the present invention.

FIGS. 7A and 7B illustrate a physician profile web page according to the present invention.

FIG. 9 illustrates a "respond to a consult" web page according to the present invention.

FIG. 10 illustrates a patient web page according to the present invention.

DETAILED DESCRIPTION OF THE INVENTION

The present invention provides for methods and systems for patient referral. The present invention provides for an internet or intranet web site that allows health care providers to interact concerning patient referrals for consultation.

Figure 1A:
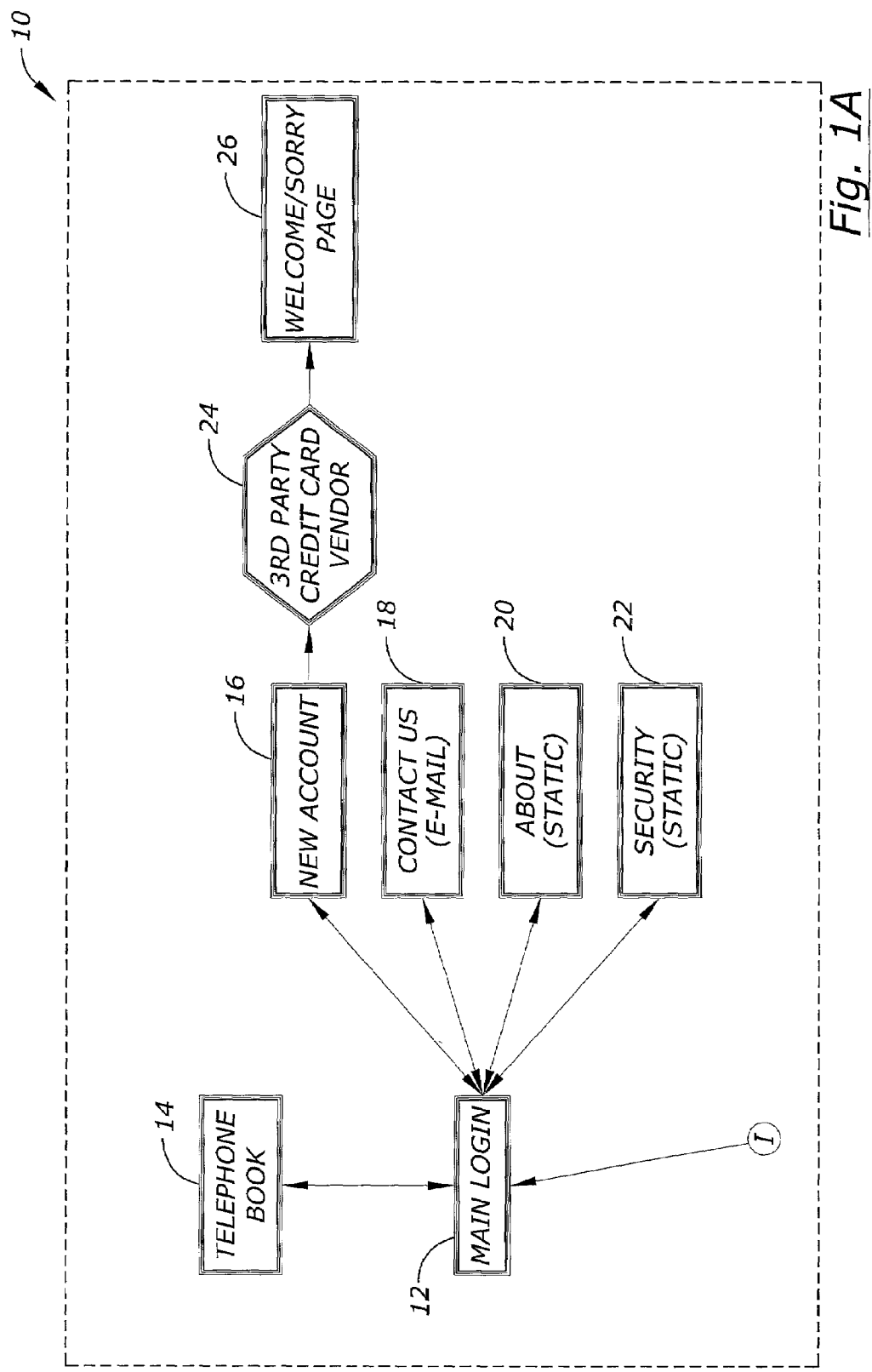
FIGS. 1A through 1C provide a flow chart illustrating the main web flow of a preferred patient referral system according to the present invention.
Figure 1B:
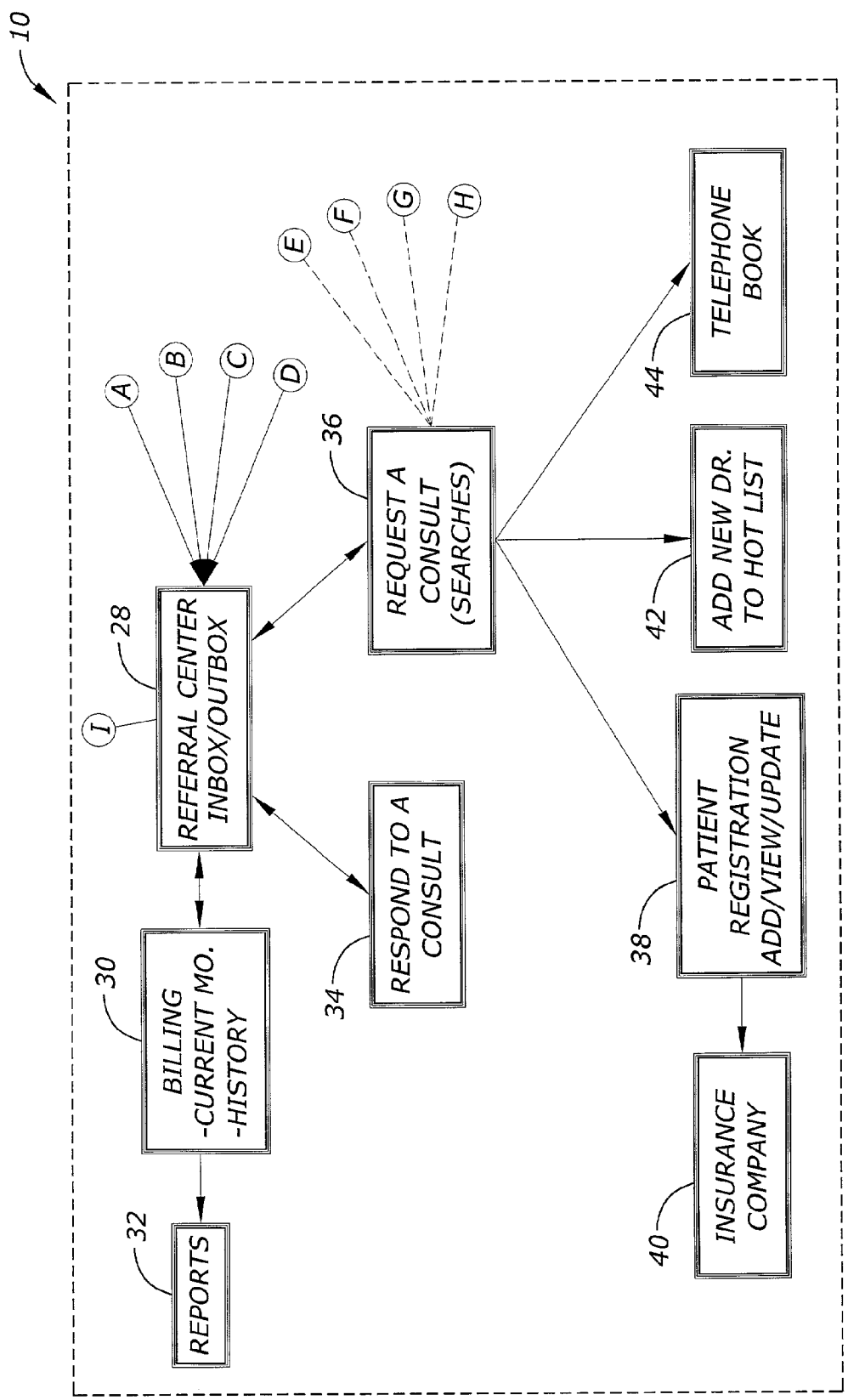
Figure 1C:
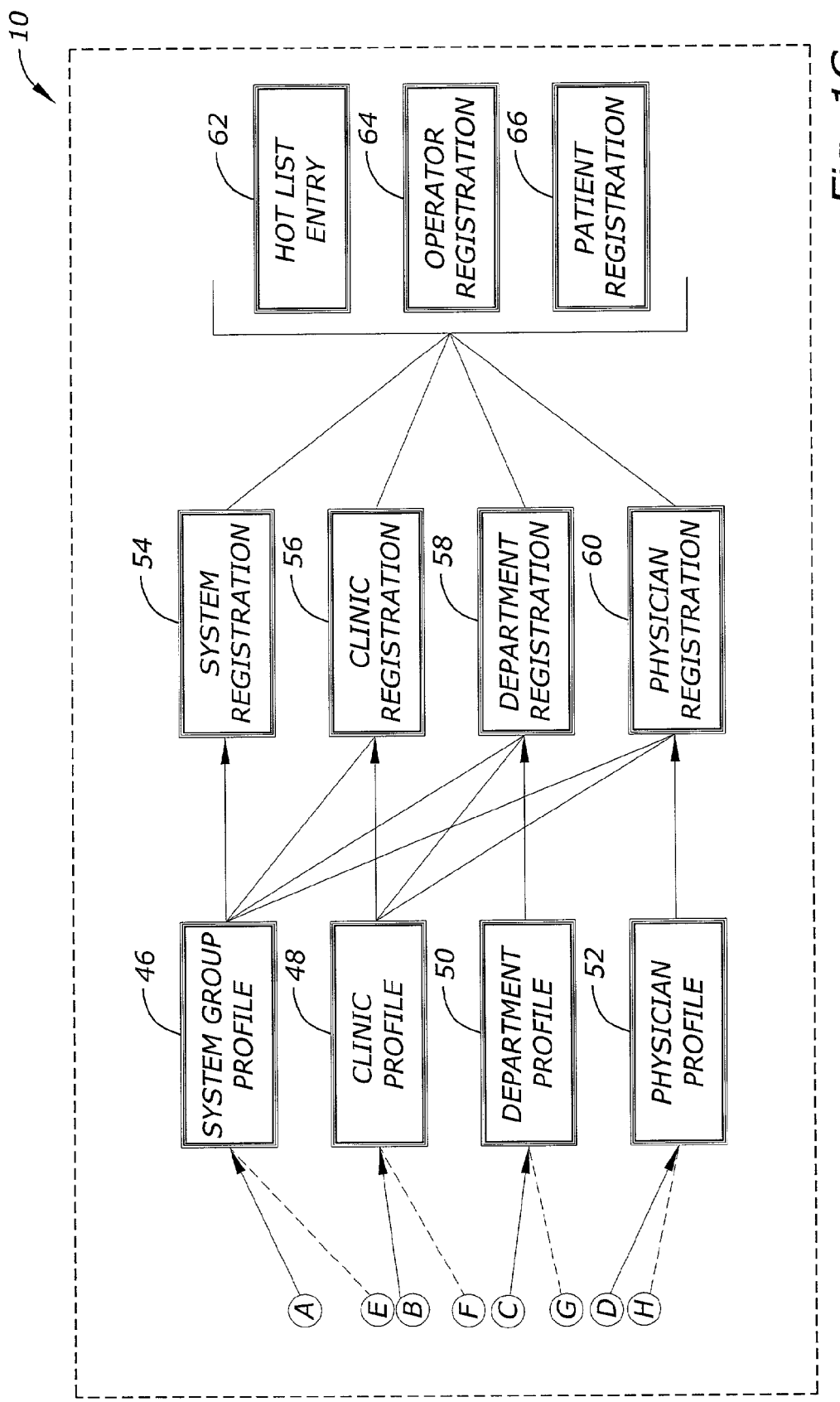

FIGS. 1A through 1C illustrate the web flow of one system according to the present invention. In FIGS. 1A-1C, the web site 10 is shown. Referring to FIG. 1A, the web site 10 includes a "main log-in" web page 12. The "main log-in" web page 12 provides for secure access to the web site. Secure access can be implemented through Secure Sockets Layer (SSL) or other secure protocols or secure methods. From the "main log-in" web page 12, access can be provided to a "telephone book" web page 14 that provides directory listings for healthcare providers. The present invention provides for this information to be accessible to patients or others who seek information about the health care providers that are registered within the system. The present invention contemplates that the "telephone book" web page 14 can include not only contact information, but maps to clinics, links to maps, and other information that may be useful to patients, health care providers, or others. From the "main log-in" web page 12, a "new account" web page 16 can also be accessed, an email contact link 18 can be accessed, information about the web site can be accessed through an "about" web page 20, and information about privacy and/or security can be accessed through a "security" web page 22.

The "new account" web page 16 allows a healthcare provider such as a physician, a department of a clinic, a clinic, or a system to create a new user account. This includes elicitation of certain information, the information may include credit card information or other billing information. The present information contemplates that users of the system may be charged for their use of the system based on their usage of the system, a set fee, or otherwise. Where credit card information is collected, a third party credit card vendor 24 is used to determine whether credit is approved or denied. A resulting web page 26 is shown welcoming the user to the web site if credit information is approved. If the information, including credit card information is not approved then the resulting web page 26 indicates that the creation of a new account has been denied. The present invention fully contemplates that other types of payment arrangements may be made and that additional approval processes may be required.

The present invention contemplates that multiple types of users can access the web site 10 of the present invention. For example, a user may be a system, clinic, department, physician, or operator. Each of these different types of users can be considered to have its own level or access level within the web site 10. Users at each of the first four levels (system, clinic, department, and physician) are considered administrators and have full access to profile information as well as in/out box information for the level of the user as well as any of the levels below it. For example, someone logging in at a system level would have access to each clinic within the system, each department within each clinic, and each physician within each department. An operator user is limited to view-only rights for profile information and has full in/out box access for the levels it has been assigned. An operator user can be assigned at various levels. There can be multiple operators for the same level, or there can be multiple operators that split scheduling duties for various departments within a clinic, or for various physicians within a department. Operator users can be staff members responsible for scheduling and other duties. Thus the present invention allows this type of operator to have limited rights but not full access privileges. The present invention provides for access through entering of a log-in ID and password that are then validated. Once access has been approved, as shown in FIG. 1B, a referral center in-box/out-box web page 28 is shown.

Figure 2:
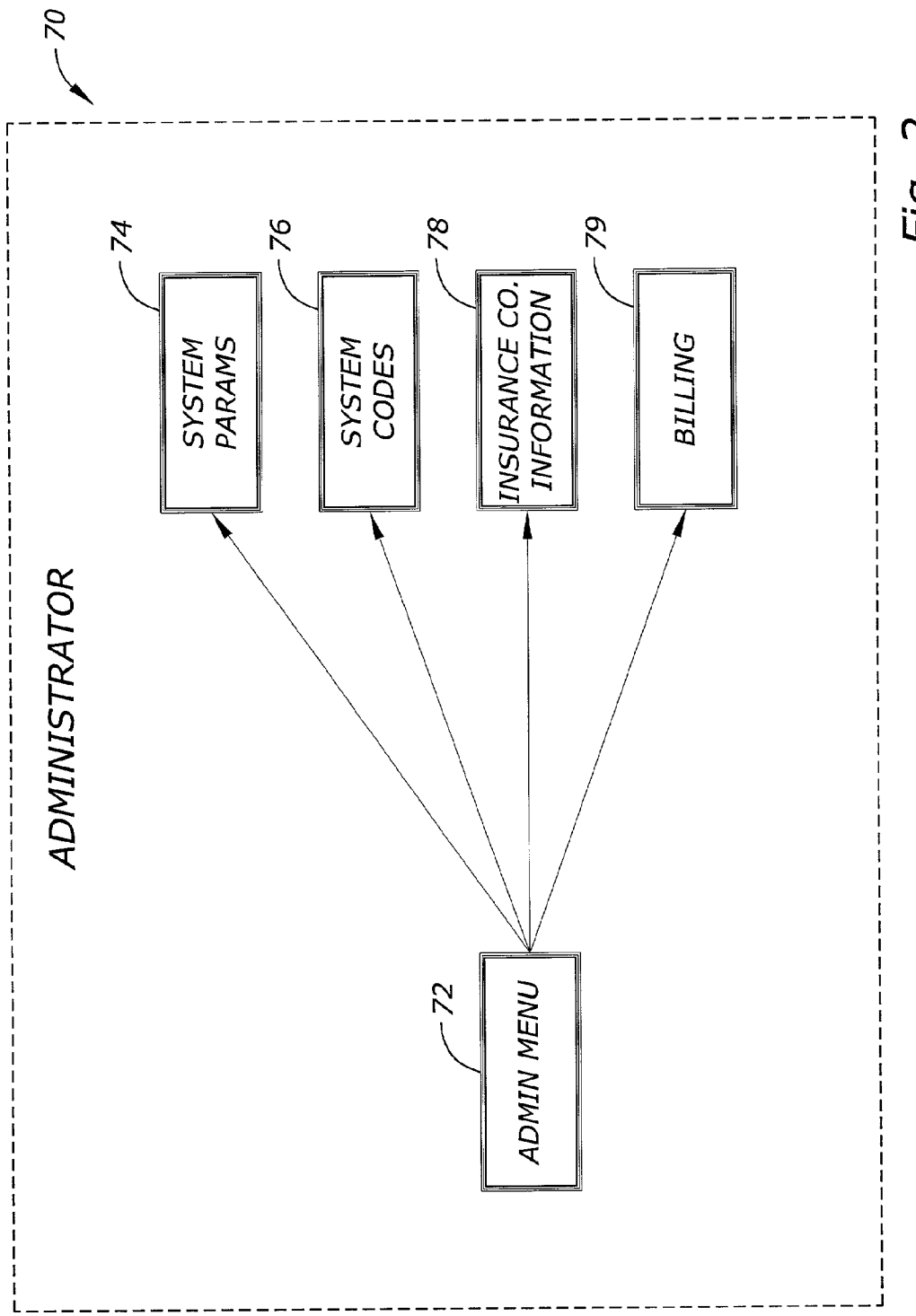
FIG. 2 provides a flow chart illustrating the main web flow of the administrative portion of a web site according to the present invention.

In addition to these various levels, the present invention further provides for a web site administration portion 70 of the web site as shown in FIG. 2. The web site administration portion 70 of the web site allows a web site administrator to perform various functions. The web site administrator portion 70 of the web site includes an "administration menu" web page 72 from which a web site administrator can select a "system parameters" web page 74, a "system codes" web page 76, an "insurance company information" web page 78, and a "billing" web page 79 or other administrative web pages that may be desired or convenient given a specific implementation of the invention.

The "system parameters" web page 74 allows the web site administrator to set basic fee amounts and/or per transaction fee amounts, whether the referring health care provider is charged or the consulting health care provider, or both, as well as other system parameters. The "system codes" web page 76 allows a web site administrator to set state codes, insurance type codes, status codes, group system types, specialty types, priority codes, preferred time codes, confirmation codes, test types, and other codes that may be convenient or desired for a specific implementation of the invention. The "insurance company information" web page 78 allows a web site administrator to create a list of insurance companies that is used by other web pages to provide a selection list. The "billing" web page 79 allows a web site administrator to review periodic billing statements, or other reports. The present invention contemplates that numerous administrative functions can be provided, those described herein are merely illustrative.

Figure 8:
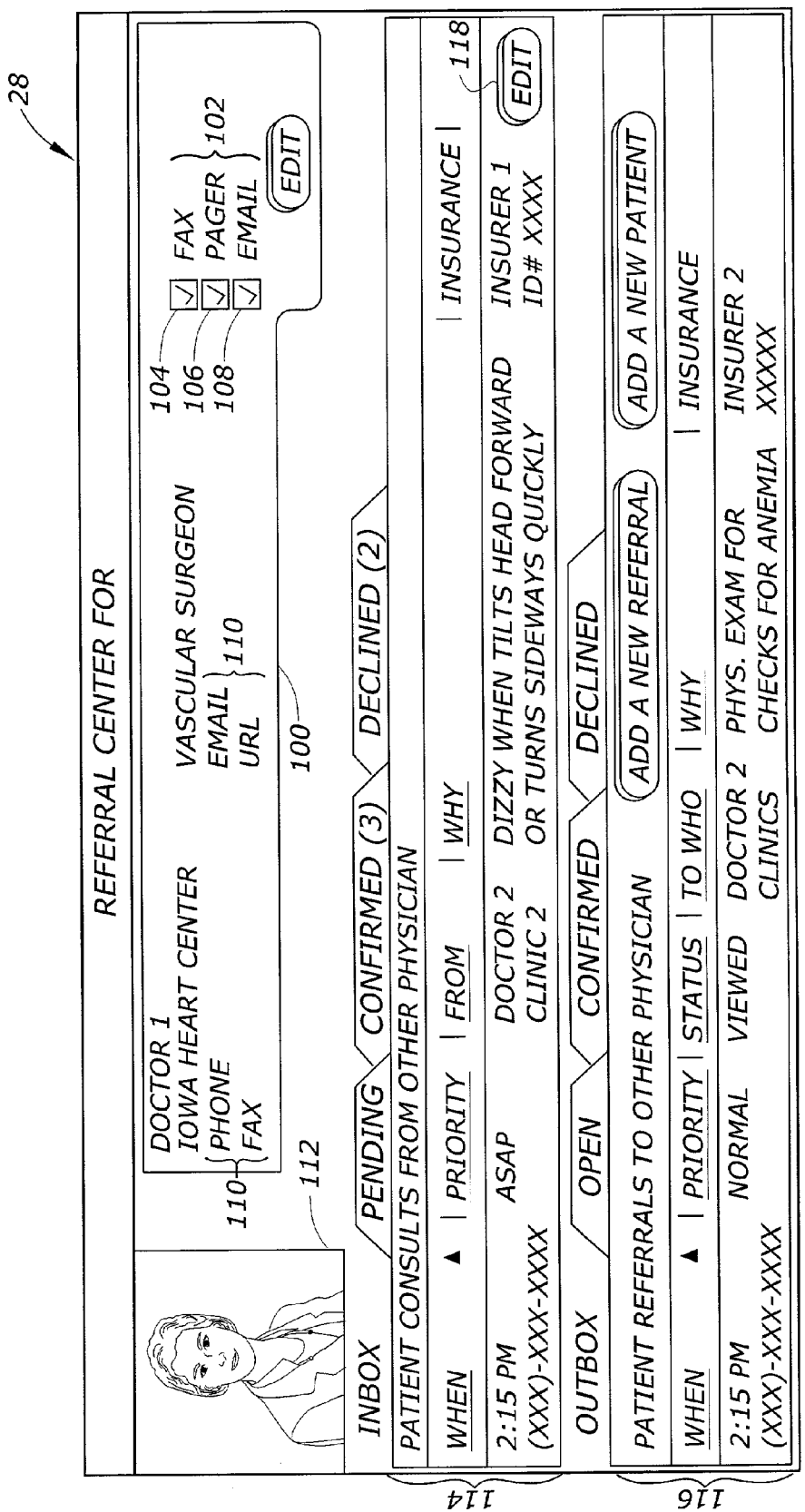
FIG. 8 illustrates a "referral center" web page according to the present invention.

Returning to the main portion of the web site, once a user has successfully logged in, the "referral center inbox/outbox" web page 28 is displayed. The "referral center in-box/outbox" 28 is best shown in FIG. 8. The referral center web page 28 includes physician information 100. The physician information 100 can include mode of communication settings 102 for the mode of communications preferred by the physician. The mode of communications can include by fax 104, by pager 106, and/or by email 108. At any time, the physician or others having access can edit these preferences to select one or more modes of communication 102 for communicating with other healthcare providers. In addition, contact information 110 is also shown and can be edited. The contact information can include a phone number, fax number, email, pager, and/or other contact information. In addition, information concerning the clinic and/or department of the healthcare provider can be shown as well as information concerning any specialty or specialties of the healthcare provider. Further, a photo or image 112 of the healthcare provider can also be shown. The referral center web page 28 includes an in-box 114 and an out-box 116. The in-box 114 contains patient consults from other healthcare providers. These patient consults can include pending patient consults that have not yet been confirmed or declined, confirmed patient consults, and declined patient consults. For each patient consult, information concerning when the request for a patient consult was made and the name and contact information for the healthcare provider who made the referral is provided. In addition, insurance information for the patient for whom a consult is requested is provided. In addition, the information in the in-box can contain a priority for each request for a patient consult. The priority can be "ASAP", "normal", or any other number of descriptions for priority. Further, the request for patient consult provides reasons why the patient consult is being requested. The healthcare provider can then access complete information for each requested patient consult and confirm or decline consultation.

The out-box 116 contains patient referrals to other healthcare providers. It also allows a healthcare provider to "add a new referral" or "add a new patient." Each patient referral can include information such as the time when the referral was made, the priority to be given to the referral, the status of the referral, to whom the referral was made, the reasons why the referral was made, and insurance information for the patient for whom the referral was made.

From the in-box 114, a user can elect to respond to a consult, such as by selecting the "edit button" 118. When a user elects to respond to a consult, the "respond to a consult" web page 34 is shown. The "respond to a consult" web page 34 is best illustrated by FIG. 9. A physician can use web page 34 to accept or deny a request for a consult. The information provided to the physician includes the date, time, priority, referring healthcare provider, preferred method of communication for their referring healthcare provider, and information concerning the reason for the requested consult. Further, the "respond to consult" web page 34 includes patient demographics information such as the patient name, address, and birth date, as well as full contact information for the requesting healthcare provider. In addition, the "respond to a consult" web page 34 includes request preferences specified by the referring healthcare provider. These requests preferences include the urgency of the request, a statement of the request as well as any comments concerning the request, and the time the request was made. The consulting healthcare provider can select a date that the requested information was sent, the method by which the requested information was sent and may then indicate that the request has been completed.

Returning to FIG. 2A, from the referral center in-box/out-box web page 28, a healthcare provider can also select to request a consult through access to a "request a consult" web page 36. The "request a consult" web page 36 is best shown in FIGS. 6A-6C. Generally, this information can be broken down into three types of information or three steps. These include specifying the patient to be referred to another clinic or physician, selecting the clinical physician with whom the referring physician wants a consult, and scheduling the consult. As shown in FIG. 6A, the patient may be searched for by name or social security number, or a new patient may be added, as shown in the search for patient information section 82. More complete patient demographic data is displayed in the patient information section 84. A new patient can be added such as through completion of a patient registration web page 38 of FIG. 10. Once a patient to refer has been added or otherwise selected, a consulting physician or clinic is selected as shown in FIG. 6B. The clinic or physician may be selected from a clinic hot list 86. Alternatively, in the clinic search portion 88, a clinic may be searched for and found. As shown in FIG. 6C, the consult may be scheduled, and preferences and consult details may be provided. These details may include the urgency of the consult, specific information concerning the precise request, any comments regarding the specific request, and the mode of notification which may include fax, pager, or email notification.

The present invention contemplates that various other web pages can be accessed through the request to consult web page 36. This is shown in FIG. 1B. For example, a "patient registration" web page 38 can be accessed. This web page allows a clinic or physician to add, view, or update patient information. This web page 38 is also shown in FIG. 10. As shown in FIG. 10, this patient web page 38 allows patient demographic information such as name, address, contact information, birth date, age, social security number, and other comments to be collected.

Returning to FIG. 1B, the web site also provides for a web page 42 to allow additional physicians or clinics to be added to a hot list of physicians or clinics. Further, a telephone book 44 can be accessed through the request a consult web page 36 in order to facilitate the process of searching for a physician or clinic to whom a consult should be requested. The present invention also contemplates that an insurance company web page 40 can be accessed through the patient registration web page 38 to provide additional information concerning insurance of a patient.

Through the insurance company web page 40 or otherwise, the present invention provides for a communication link with each registered insurance company and all of its registered health care providers. Through linkage with an insurer, the present invention also provides for the procurement of authorization codes via an automatic electronic request to an insurance company. The process is expedited as the insurer is instantly provided with all of the information necessarily required to approve the referral. All concerned parties are immediately notified of approval or denial. Authorization numbers and denial information can be automatically tracked and stored. This information is then available for further reference to avoid and resolve reimbursement issues. The procurement of an authorization code from an insurance company preferably occurs in the background after a referral request is made and eliminates the need for ongoing office documentation and time-consuming telephone calls.

Figure 7A:
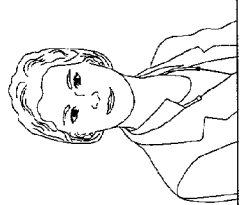

Also accessible from the referral center in-box/out-box 28, as shown in FIGS. 1A and 1C, are profile web pages. These profile web pages can include a system group profile page 46, a clinic profile page 48, a department profile page 50, and a physician profile page 52. Each profile page includes information profiling a system, clinic, department, or physician. FIG. 4 provides an illustration of a clinic profile web page 48. Clinic information can include contact information as well as payment information, such as credit card information. Each clinic profile can include a list of physicians affiliated under the clinic, a list of departments under the clinic, a list of operators under the clinic. FIGS. 7A and 7B show a physician profile web page 52 according to the present invention. This information can include personal information concerning a physician including contact information, medical license information, and other information. Further, this physician profile web page 52 can include a photograph or image of the physician, information concerning the clinic associated with the physician, as well as other information. For example, the physician profile web page 52 can include the number of requests for consults made, the number of consults performed, and the number of active consults which have not yet been performed. As shown in FIG. 7B, this web page can show preferences for the mode of notification such as fax, pager, and/or email. Further, this web page can include feedback, survey results, or other forms of a peer review component related to the physician. This peer review component can include comments made by those physicians who have requested consults from the physician. Thus, a physician can access his or her profile to see a peer review. This provides a useful tool for analyzing or reviewing a physician's relationship with those who refer patients. Each of the set of referral feedback information 150 can be either anonymous or attributed to a referring physician. This provides a physician, particularly a consulting physician, with some measure or evaluation of their client relations. An example of such a physician profile is shown in FIGS. 7A and 7B. In FIG. 7B, comments concerning the physician are shown.

The preferred embodiment includes a new patient referral system designed and developed using a multi-tiered, component architecture. The component-based framework of the preferred embodiment includes distinctive service layers that can be distributed across multiple physical tiers. The service layers of the preferred embodiment include presentation services, user services, business services, data services. Those skilled in the art recognizes that following such a multi-tiered approach allows new components and services to be added without disrupting existing functionality.

The software architecture for the patient referral system follows the Microsoft windows Distributed interNetworking Applications (DNA) architecture. It is accessed and executed as a browser-based application over the Internet. Although the present invention contemplates that an Intranet may also be used. The "work" components forming user services, business services, and data services are preferably hosted on a Microsoft Transaction Server (MTS), and the presentation components are hosted on a web server running Microsoft Internet Information Server (IIS). The back-end database is either DB2 or oracle.

The software is written in Microsoft Visual Basic (VB) using Web Class technology, Structured Query Language (SQL) is embedded in the VB code to access the underlying data. Other technologies include HTML and JavaScript.

The precise operating system and hardware configurations are not limited to any specific hardware or software configurations. Those skilled in the art will recognize that the software, system, and methods of the present invention can be implemented on a wide variety of hardware and software platforms.

Thus, a system and methods of a client referral system have been disclosed. The present invention contemplates numerous modifications, changes, and variations. These variations include variations in the types and amounts of data collected, the specific hardware and software implementations used, any number of user interfaces used, variations in the organization and structure of the web site, and other modifications, changes, and variations.

What is claimed is:

1. A method of managing patient referrals, comprising:
   providing a web site accessible to a plurality of health care providers;
   receiving through the web site, a plurality of health care provider registrations each associated with a health care provider;
   receiving a request for a patient consultation from a first health care provider to be performed by a second health care provider, both the first health care provider and the second health care provider having a health care provider registration;
   notifying the second health care provider of the request for a patient consultation according to a preferred mode of communication setting set by the second health care provider on the web site; and receiving a peer rating from the first health care provider of the second health care provider.

2. The method of claim 1 further comprising receiving a response from the second health care provider accepting or declining the request for a patient consultation.

3. The method of claim 2 further comprising scheduling a time for the patient consultation.

4. The method of claim 1 wherein the peer rating is anonymous.

5. The method of claim 1 wherein the peer rating is attributed to the first health care provider.

6. The method of claim 1 further comprising providing the peer rating to the second health care provider.

7. The method of claim 1 further comprising providing a health care provider profile associated with a health care provider registration.

8. The method of claim 1 wherein the request for patient consultation includes patient demographic data.

9. The method of claim 1 wherein the request for patient consultation includes insurance information.

10. The method of claim 1 wherein the request for patient consultation includes patient contact information.

11. The method of claim 1 wherein the request for patient consultation includes appointment preference information.

12. The method of claim 1 further comprising providing information concerning the request for patient consultation to an insurer.

13. The method of claim 12 further comprising receiving notification of approval or denial from the insurer.

14. The method of claim 1 wherein the step of notifying is notifying via email.

15. The method of claim 1 wherein the step of notifying is notifying via fax.

16. The method of claim 1 wherein the step of notifying is notifying via paging.

17. A system for managing patient referrals, comprising:
a web site accessible to a plurality of health care providers;
at least one registration web page within the web site to allow each of the plurality of health care providers to register to become registered health care providers;
an inbox within the web site associated with at least one of the registered health care providers and containing at least one request for a patient consult made to the at least one of the registered health care providers;
an outbox within the web site associated with the at least one of the registered health care providers and containing at least one request for a patient consult made by the at least one of the registered health care providers;
a peer review component for providing feedback related to a patient consult by a consulting health care provider from a referring health care provider;
a mode of communication preference set by a referring health care provider and provided to a consulting health care provider.

18. The system of claim 17 wherein the at least one registration web page includes a physician registration web page.

19. The system of claim 17 wherein the at least one registration web page includes a clinic registration web page.

20. The system of claim 17 wherein the at least one registration web page includes a department registration web page.

21. The system of claim 17 further comprising a patient registration web page.

22. A method of managing patient referrals, comprising:
providing a web site accessible to a plurality of health care providers, the plurality of health care providers including a referring physician and a consulting physician;
receiving a request on the web site from the referring physician for a patient consultation to be performed by the consulting physician on a patient;
notifying the consulting physician of the request for a patient consultation;
requesting an authorization number for the patient consultation from an insurer providing insurance to the patient;
wherein the step of notifying the consulting physician is notifying the consulting physician according to a preferred mode of communications setting set by the consulting physician on the web site.

* * * * *